(12) United States Patent
Oxley et al.

(10) Patent No.: US 6,174,720 B1
(45) Date of Patent: Jan. 16, 2001

(54) MODIFIED BIOREACTOR

(75) Inventors: John Oxley, West Yorkshire (GB); Joseph Francis Startari, Clearwater, FL (US)

(73) Assignee: Biotechna Environmental International Limited, The Valley (AI)

( * ) Notice: Under 35 U.S.C. 154(b), the term of this patent shall be extended for 0 days.

(21) Appl. No.: 09/308,458

(22) PCT Filed: Sep. 21, 1998

(86) PCT No.: PCT/GB98/02846

§ 371 Date: May 19, 1999

§ 102(e) Date: May 19, 1999

(87) PCT Pub. No.: WO91/15620

PCT Pub. Date: Apr. 1, 1999

(30) Foreign Application Priority Data

Sep. 19, 1997 (GB) .................................................. 9719965

(51) Int. Cl.[7] ...................................................... C12M 1/00
(52) U.S. Cl. ...................... 435/293.1; 435/383; 435/420; 435/293.2; 435/295.2
(58) Field of Search .................................... 435/383, 420, 435/289.1, 292.1, 293.1, 293.2, 295.2

(56) References Cited

U.S. PATENT DOCUMENTS 5,137,828 * 8/1992 Robinson et al. .

FOREIGN PATENT DOCUMENTS

| 297 06 379 U | * | 8/1997 | (DE) . |
| WO 94 11094 | * | 5/1994 | (WO) . |
| WO 95 06111 | * | 3/1995 | (WO) . |

* cited by examiner

Primary Examiner—David A. Redding
(74) Attorney, Agent, or Firm—Fay, Sharpe, Fagan, Minnich & McKee, LLP

(57) ABSTRACT

Bioreactor apparatus for culture of living matter in a liquid medium includes a plurality of tubes connected at one end to a primary manifold section and at their other end to a secondary manifold section such that a flow of liquid containing the living matter can be established within the manifolds and tubes. The flow of liquid medium in such manifolds and/or tubes is capable of control by at least one gas injection device in communication with the primary manifold section and at least one gas injection device in communication with the secondary manifold section. Such an arrangement provides finer control of the flow conditions in the tubes forming part of the bioreactor and of the environmental conditions for culture of the living matter. The arrangement can have a relative simplicity of design which also permits a reduction in the total number of tanks and/or control loops usually associated with bioreactor apparatus of this type.

9 Claims, 4 Drawing Sheets

MODIFIED BIOREACTOR

This invention is concerned with bioreactors for the commercial culture of micro-organisms. In particular the invention is concerned with improvements in tubular-type photobioreactors.

Coiled, tubular photobioreactors are known and an example of one such photobioreactor, with which the present invention finds application is disclosed in U.S. Pat. No. 5,137,828. The present invention is, however, not limited to application in that precise form of coiled, tubular photobioreactor, since embodiments of the present invention have application in other tubular bioreactors whether coiled, straight line, meandering or segmented. Meandering such reactors are presently in use in, for example, Germany and Israel.

Coiled, tubular photobioreactors of the type illustrated in U.S. Pat. No. 5,137,828 are commercially available under the BIOCOIL trade mark. It will be of assistance to the reader to have a background knowledge of such a bioreactor and in particular the embodiment of FIG. 4 in the said U.S. Patent wherein a plurality of coiled, tubular segments are in liquid communication via a pair of generally upright manifolds, identified in FIG. 4 as items 57 and 56 respectively.

Segmented coil tubular bioreactors of this type (incorporating a pair of manifolds linking together a plurality of individual, coiled segments) are known and commercially available from the applicants herein. The present invention has been devised by way of an improvement in tubular bioreactors which is particularly effective in the culture of such living matter as algae or bacteria due to the low stress induced by a gas lift system.

An arrangement of coiled, tubular photobioreactor incorporating an upright manifold is known wherein the manifold serves to link the upper part of a coil in liquid communication with the lower part of the coil and wherein such manifold is subjected to gas injection flow enhancement. Such apparatus is known as the 'single air lift' BIOCOIL (trade mark) photobioreactor.

Apparatus incorporating an air lift system were devised for the handling of specific algae systems where pumping is inappropriate for one reason or another.

However, we have found that single air lift manifold photobioreactors are relatively inefficient in the stripping of oxygen from circulating liquor and liquid circulation control within each individual coiled segment of the photobioreactor is particularly limited.

According to the present invention we provide bioreactor apparatus for culture of living matter in a liquid medium comprising a plurality of tubes connected at one end to a primary manifold section and at their other ends to a secondary manifold section such that a flow of liquid containing said living matter can be established within said manifolds and tubes, wherein the flow of liquid medium in said manifolds and/or said tubes is capable of control by at least one gas injection means in communication with the primary manifold section and at least one gas injection means in communication with the secondary manifold section.

The tubes are preferably arranged so that the helix angle allows gaseous products to be carried out of the coils. Instead of one coil above the other, the coils could be in grouped batches.

Preferred features of the apparatus are also to be found in the sub claims. We also provide methods of culturing living matter which involves use of the present apparatus.

In a preferred embodiment applicable to a coiled, tubular bioreactor we also provide bioreactor apparatus including at least two generally tubular coils wound helically, to give a helix angle which allows gaseous products to be carried out of coils located one above the other or in grouped batches around an upstanding support structure, the coils having inlets to receive a flow of liquid medium within which biomass or other living material can be cultured and an outlet for said medium, the inlets of the coils arranged in liquid communication with a primary manifold and the outlets of the coils arranged in liquid communication with a secondary manifold, both said manifolds being in liquid communication whereby a flow of liquid medium can be provided from the primary to the secondary manifold, primary flow control means being provided to act upon liquid medium in or flowing from the primary manifold and secondary flow control means provided to act on liquid medium in or flowing into the secondary manifold, the primary and secondary flow control means being adjustable whereby flow of liquid medium through the coils can be varied by adjustment of either or both said flow control means.

Preferred advantageous features of the present apparatus and its use will now be described in the specific embodiments hereunder.

In order that the invention may be more easily appreciated and readily carried into effect by one skilled in this art, embodiments thereof will now be described purely by way of example only, with reference to the accompanying drawings and wherein:

BRIEF DESCRIPTION OF DRAWINGS

As shown in FIGS. 1 and 2 a coiled photobioreactor is based upon a generally cylindrical support structure 13 around which individual coils (not shown separately) are wound helically and through which a flow of liquid medium can be established. An inlet 11 of a first (highest) tubular coil is shown connected in liquid communication with a primary manifold 5. Beneath the said inlet 11 there are a series of inlets for other coils all of which are similarly connected to this primary manifold 5 in liquid communication. The primary manifold 5 essentially consists of a generally hollow tube or pipe which is located generally upright and preferably vertical or near vertical, secured if required to the support structure 13. The outlets of the coils are similarly connected in liquid communication to a secondary manifold 1 the outlet 12 of the first coil being shown, at the upper part of this secondary manifold 1. In similar fashion to the arrangement of inlets, the outlets are also located generally one above the other all being in liquid communication with the said secondary manifold 1. A batch of liquid media feed stock is supplied from a source 18 which feed comprises nutrients essential for growth of the algae or other micro organisms to be cultivated within the apparatus, the supply leads to a tank 19 from where it is pumped by means of pump 33 along a supply line 20 (monitored by flow meter 27) to an inlet port 14 for the media solution on manifold leg 5 above the uppermost coiled segment of the photobioreactor. The inlet could be at another location. Liquid is then supplied to all coiled segments of the bioreactor apparatus by means of the primary manifold 5 passing to the secondary manifold 1 (which are in the nature of generally upright hollow tubes) and which are linked in this embodiment by three further tubular extension pipes. Pipe 4 leads from a second header tank 9 located at the upper part of that extension pipe 4, the extension pipe 4 being linked by means of a connecting piece 17 to a second upright extension pipe 3 which leads into a first header tank 7 and from which tank descends a third extension pipe 2 connected at its lowermost end by connecting piece 16 to the secondary manifold 1. Any part of the coiled segments can be cooled, if required, by using a supply of cooling water 31 which can be pumped to or around the support structure 13, or liquid medium containing the cultured micro-organism can be cooled through an inline cooler of a type which allows for easy cleaning.

Figure 1:
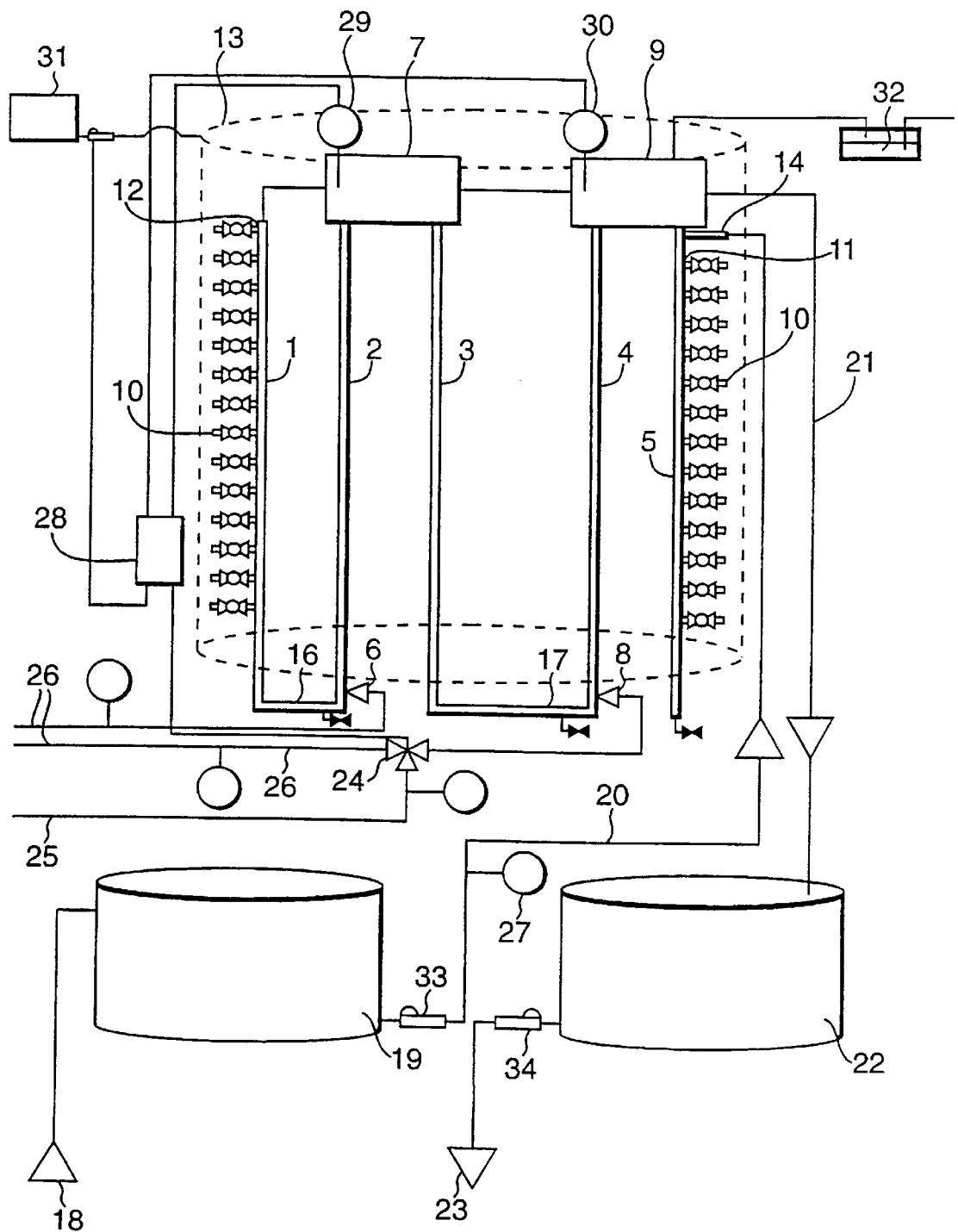
FIG. 1 is a schematic representation of a bioreactor apparatus according to the invention using two separately controllable gas inlets for flow enhancement.

The temperature of the liquid medium flowing through the bioreactor can be monitored by means of a thermometer or other temperature monitor 29 and the acidity/alkalinity of the liquid medium can be monitored by means of a pH meter 30 a probe of which is located in the second header tank 9. Both the temperature and pH can be controlled by means of a pH and temperature controller 28 which is linked to a $CO_2$ supply and cooling water supply means 31. The control of pH could alternatively or additionally be made by the addition of suitable acid or base. This could be achieved instead of control of pH by $Co_2$ injection, at the same addition point.

Liquid medium containing the cultured micro organism e.g. algae, bacteria or similar living matter which has been innoculated into the liquid medium, can be drawn off at a convenient location e.g. from the second header tank 9 by means of a take off line 21 which communicates with a product tank 22, the contents of which can be transferred by means of pump 34 to a product outlet point 23. At this point the cultured living matter can be used as is, diluted or isolated from the liquid medium, washed, purified or further processed according to requirements.

Means 24, such as valve means, are provided to which two different supplies of gaseous media are connected. Air lines 26 and a $CO_2$ line 25 lead into this means 24 and the flows of gases can be monitored by means of flow meters F1A and F1B. From the means 24 there is a gaseous media injection point 8, acting as secondary flow control means at the lower end of the third extension pipe 4. A separate airline supplies a gaseous media injection point 6, acting as primary flow control means located in the first extension pipe 2. The gaseous injection points are in the vicinity of the base of the extension pipes and capable of delivering e.g. air and/or $CO_2$ at varying flow rates into the liquid medium which is flowing within the respective extension tubes 2 and 4. Thus primary flow control means 6 serves to act upon liquid medium flowing from the secondary manifold and secondary flow control means 8 serves to act upon liquid medium flowing into the manifold leg 4.

The arrangement and operation of the interconnected primary and secondary manifolds is more particularly described with reference to FIG. 2 where the horizontal tubes could equally be those of a straight line or fence type reactor. Liquid enters the secondary manifold 1 via a number of connections 12 from tubes 10 along its length and flows downwards in its operating mode. A gaseous fluid is injected into the flow control means 6 at the base of first extension pipe 2 and flows up the pipe to the first header tank 7 where the gaseous fluid disengages from the liquid. Design of these header tanks 7, 9 is such that they can drain completely and are constructed without sharp corners for the avoidance of regions with reduced flow and for ease of cleaning, as well as their function as a gas lift system. Further benefit and unique improvement is that these boxes and manifolds are typically sized to allow for elimination of further dark storage capacity, thereby eliminating the need for, and complexity of, an additional storage tank, and the associated capital and operating costs. Liquid essentially disengaged from gaseous fluid passes down second extension pipe 3 which is a connecting member and into the base of the pipe 4 which is part of the inverted 'U'-shaped manifold where the same or different gaseous fluid is supplied to that pipe via the secondary flow control means 8. A gaseous fluid is injected into the said pipe 4 at its base to flow up the pipe to the second header tank 9 where that gaseous fluid disengages from the liquid. Liquid essentially disengaged from the gaseous fluid passes down the remainder of primary manifold 5, being an upright tube which has a number of connections 11 which allow liquid to leave this manifold tube at several such connections simultaneously. The connections between the tube segments inlets/outlets and both manifolds may be valved or unvalved.

Typically, an air or air/$CO_2$ mixture is blown into a 'leg' of aqueous fluid in the respective pipe which has the effect of reducing the average density of the liquid in the 'leg' and the upper surface rises to balance the inlet pressure on the base of the 'leg'. The rising liquid disengages to a large extent from the gas and with this appropriate arrangement of piping flows into the top of another 'leg' down which it flows. The head generated by this method in two gaseous lift stages is then used as the motive force for moving the liquid through all the tubes 10 present in the bioreactor. The tubes 10 require a minimum flow of liquor to give adequate mixing. The header tanks are in gaseous communication at their upper ends, if required, tank 9 being in gaseous communication with an air sterilizer 32.

Typically for water in smooth tubes Reynolds numbers greater than 2,600 give a turbulent flow; adequate for good mixing. Typically the range of flows in these tubes is 2 to 3 times that required to achieve turbulent flow in water (typically this would be 25 cm/sec in a 2.5 cm tube). Flows through each coil segment, if using a coiled bioreactor, need not be identical but are preferably within 20% of the average.

The arrangement of the tubes 10 (which can be coiled segments of tube) in relation to the manifolds is such that each tubular segment within the bioreactor can be subject to almost identical pressure drop. Because the tube dimensions can be and preferably are the same for each tubular segment, the flows can be and preferably are essentially identical within each such segment. One exception is, however, the bottom segment where considerations of settlement prefer a design which gives a slightly different flow than average because of the line layout.

The gas-lift manifold design and line arrangements result in a system which does not require individual flow metering arrangements for each segment of tube thereby eliminating capital costs for these items, and is designed for ease of cleaning. Gas venting and feed arrangements are such that preferably only filtered gas enters the unit.

This particular modification of a tubular bioreactor is especially useful where flows are large, lifts are high, or more than one gas mixture is required.

An arrangement is provided offering the possibility of, for example, using air in the first stage 6 followed by the second stage 8 in which there can be a stripping gas with a reduced partial pressure of oxygen to promote stripping of oxygen from the circulating liquid. In addition other beneficial gases may be added, e.g. $CO_2$.

The apparatus has the ability to use completely different gases or gas mixtures in primary 6 and secondary flow control means 8, at differing flow rates, and the enhanced ability to strip oxygen from oxygenated flowing liquids results in improved growth rates for algae.

Figure 2:
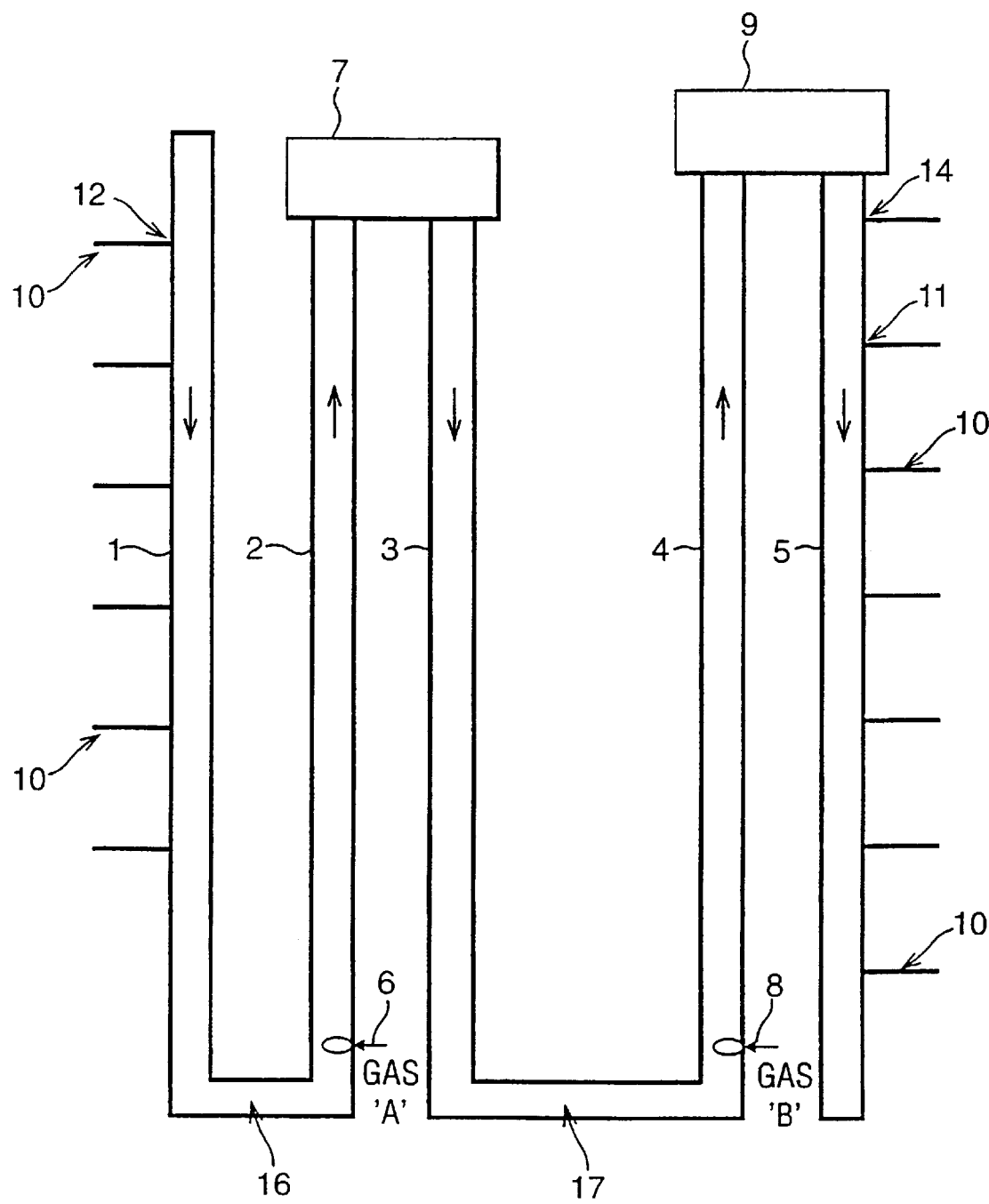
FIG. 2 is an enlarged partial section of FIG. 1 showing the manifolds and tube/manifold connections more clearly.
Figure 3:
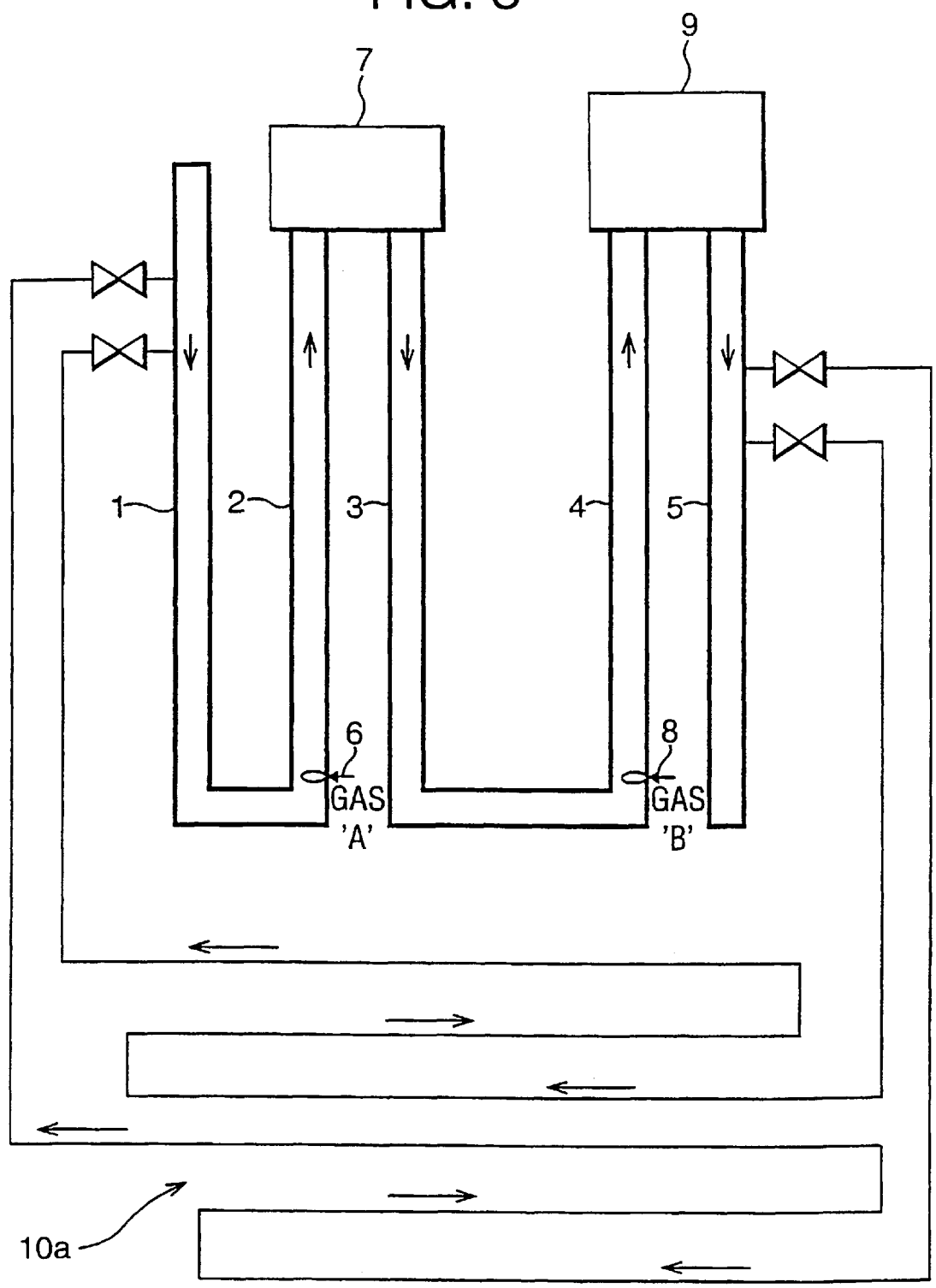
FIG. 3 is a further schematic representation of a straight line tubular reactor using the modified bioreactor apparatus, where the tubes may be horizontal and supported by external structure or at a slight incline to improve transfer of gaseous products out of the tubes.

FIG. 3 shows, schematically, an alternative arrangement still based on the FIG. 2 principles whereby instead of a number of helically wound tubes as in the FIGS. 1 and 3 coiled bioreactor embodiments, a number of tubes can be affixed to the same connections 10 as shown in FIGS. 1 and 2, but arranged in a different spatial configuration which still permits the efficient transfer of evolved gases from the tubes. As shown the main tube layout 10*a* is in the form of hairpin loops fed at one end from a primary manifold 5 and flowing to a secondary manifold 1. As an alternative, the meandering type of tubular photobioreactor could be utilized where hairpin loops are replaced with connections known as 'easy bends' instead of bending or turning the actual tubes. The apparatus will be equally effective in a meandering tube type photobioreactor. The manifolds may serve one or more horizontal tubes. The nominally horizontal sections can also conveniently be arranged on a structure for support.

The arrangement is of a double- or twin- airlift manifold with horizontal straight tubular reactor with essentially the same reference numerals as in FIGS. 1 and 2, the generally horizontal photobioreactor tubes being connected to manifold sections 1 and 5. The nominally horizontal sections of tubes actually rise slightly in the direction of flow in order to aid removal of gas bubbles evolved during photosynthesis i.e. culturing of the living matter under conditions of natural or supplementary lighting.

The header tanks and diameter of the manifolds/'legs' can be suitably proportioned to eliminate unwanted additional dark storage areas or tanks.

Figures 4, 4A:
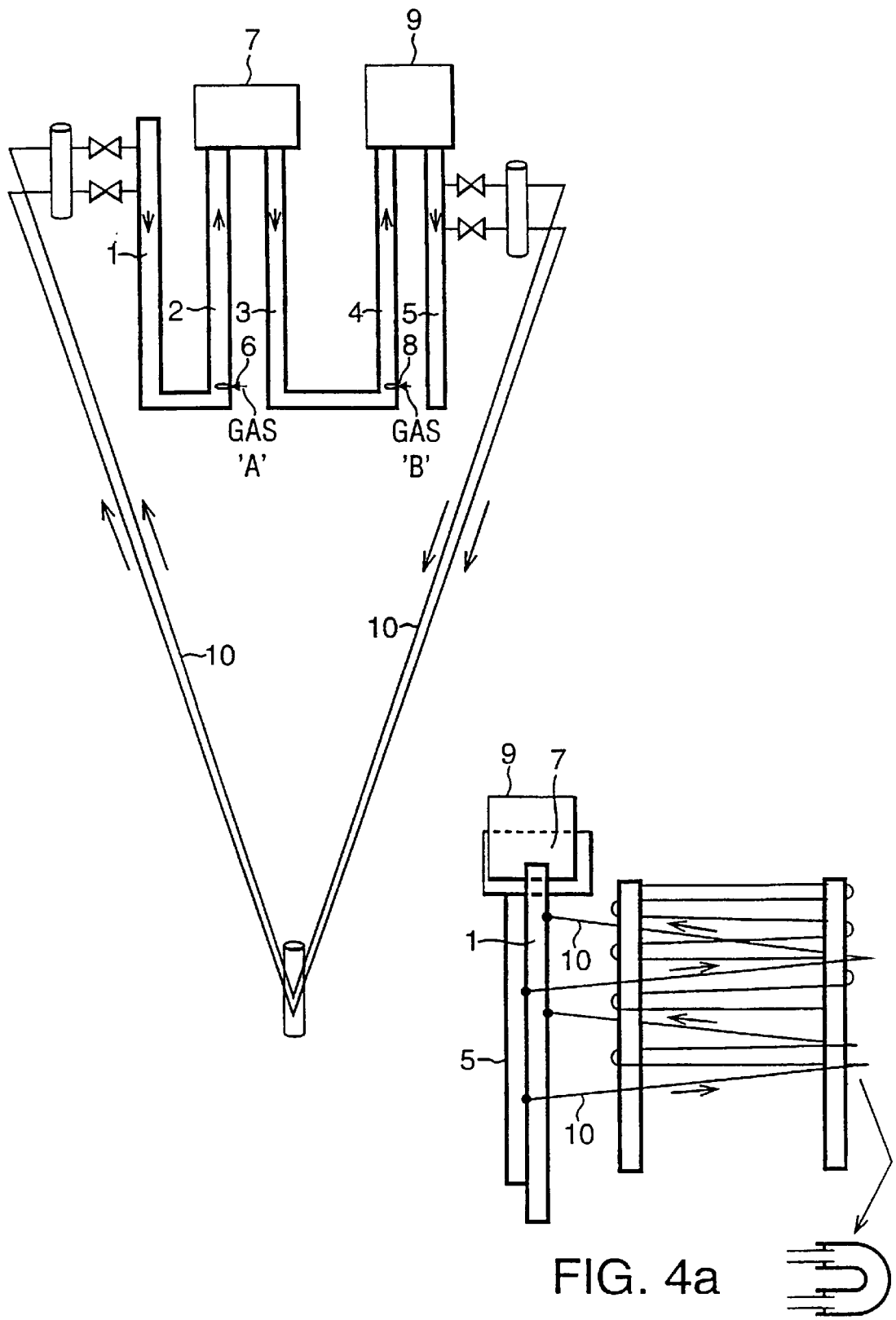
FIGS. 4 and 4a are further schematic representations of an alternative straight line tubular reactor using the modified bioreactor apparatus showing the tubes supported by a structure which may or may not be immediately adjacent.

FIGS. 4 and 4*a* show an alternative view of a straight line tubular reactor in which the support is shown unconnected to the manifold. The supports should be available along most of the length of the tubes in order to avoid distortion and intermediate high points which would mitigate against removal of oxygen from the system and reduce the effectiveness of photosynthesis.

The upright posts shown provide supports for the tubular array 10. As indicated in FIG. 4*a* the tubes need not be continuous since they can be connected by internal or external sleeves such as in this particular 'fence' type arrangement.

In place of the 'fence' type structure shown in FIG. 4*a*, the fence component can comprise of a pair of upstanding supporting posts interconnected by structural panels.

What is claimed is:

1. Bioreactor apparatus for culture of living matter in a liquid medium comprising a plurality of tubes connected at one end to a primary manifold section and at their other ends to a secondary manifold section such that a flow of liquid containing said living matter can be established within said manifolds and tubes, wherein the flow of liquid medium in said manifolds and/or said tubes is capable of control by at least one gas injection means in communication with the primary manifold section and at least one gas injection means in communication with the secondary manifold section.

2. Apparatus as claimed in claim 1 wherein each manifold section includes a header tank where gaseous media can disengage from liquid medium when flowing through said manifolds.

3. Apparatus as claimed in claim 1 wherein both primary and secondary manifold sections include at least two spaced apart upright tubular members, at least one of which is in liquid communication with said plurality of tubes.

4. Apparatus as claimed in claim 1 wherein the primary manifold section and the secondary manifold section each have at least one gas injection port in the vicinity of the lowermost region of a generally upright tubular component of said section.

5. Apparatus as claimed in claim 4 wherein each gas injection port is independently controllable as to gas used for injection and flow rates.

6. Apparatus as claimed in claim 1 wherein the primary manifold section and the secondary manifold section comprise, respectively, a U-shaped tubular arrangement and an inverted U-shaped tubular arrangement.

7. Apparatus as claimed in claim 1 wherein the primary and secondary manifold sections each comprise a pair of tubes, one located generally concentrically about the other.

8. Bioreactor apparatus including at least two generally tubular coils wound helically to permit gaseous products to be carried out of the coils located one above the other or in grouped batches around an upstanding support structure, the coils having inlets to receive a flow of liquid medium within which biomass or other living material can be cultured and an outlet for said medium, the inlets of the coils arranged in liquid communication with a primary manifold and the outlets of the coils arranged in liquid communication with a secondary manifold, both said manifolds being in liquid communication whereby a flow of liquid medium can be provided from the primary to the secondary manifold, primary flow control means being provided to act upon liquid medium in or flowing from the primary manifold and secondary flow control means provided to act on liquid medium in or flowing into the secondary manifold, the primary and secondary flow control means being adjustable whereby flow of liquid medium through the coils can be varied by adjustment of either or both said flow control means.

9. A method of culturing living material including algae, bacteria or other microorganisms comprising:

providing the bioreactor apparatus of claims 1 or 8;

providing a source of said living material to said apparatus, and operating said apparatus to culture said living material.

* * * * *